United States Patent
Lasky et al.

[11] Patent Number: 5,854,012
[45] Date of Patent: Dec. 29, 1998

[54] COMPOSITION, METHOD AND APPARATUS FOR SAFE DISPOSAL OF OIL CONTAMINATED FILTER

[75] Inventors: William M. Lasky, Charlotte; James H. Cornwell, Wilmington, both of N.C.

[73] Assignee: Dana Corporation, Toledo, Ohio

[21] Appl. No.: 992,510

[22] Filed: Dec. 17, 1997

[51] Int. Cl.⁶ ............................. C12Q 1/02; G01N 33/53
[52] U.S. Cl. ...................... 435/29; 435/975; 435/244; 436/29
[58] Field of Search .................. 435/29, 975, 244; 436/29

[56] References Cited

U.S. PATENT DOCUMENTS

| | | | |
|---|---|---|---|
| 2,396,900 | 3/1946 | Taggart, Jr. | 435/334 |
| 3,220,928 | 11/1965 | Brenner | 435/264 |
| 3,347,297 | 10/1967 | Garland | 435/29 |
| 3,532,599 | 10/1970 | Cooperman | 435/29 |
| 3,843,517 | 10/1974 | McKinney et al. | 435/281 |
| 4,111,813 | 9/1978 | Preus | 435/29 |
| 4,446,236 | 5/1984 | Clyde | 435/29 |
| 4,530,763 | 7/1985 | Clyde et al. | 435/29 |
| 4,689,301 | 8/1987 | Adet et al. | 435/29 |
| 4,850,745 | 7/1989 | Hater et al. | 435/29 |
| 4,988,443 | 1/1991 | Michaels et al. | 435/29 |
| 5,344,557 | 9/1994 | Scanzillo | 435/29 |
| 5,376,183 | 12/1994 | Gatt et al. | 435/29 |
| 5,395,535 | 3/1995 | Pinckard | 435/29 |
| 5,415,777 | 5/1995 | Krempen et al. | 435/29 |
| 5,458,773 | 10/1995 | Holland | 435/29 |
| 5,541,096 | 7/1996 | Nomura et al. | 435/29 |
| 5,589,004 | 12/1996 | Lashmett et al. | 435/264 |

FOREIGN PATENT DOCUMENTS

| | | |
|---|---|---|
| 0 255 354 | 2/1988 | European Pat. Off. . |
| 7-116514 | 5/1995 | Japan . |
| 2 159 834 | 12/1985 | United Kingdom . |
| 94/23802 | 10/1994 | WIPO . |

*Primary Examiner*—Louise N. Leary
*Attorney, Agent, or Firm*—Millen, White, Zelane, & Branigan, P.C.

[57] ABSTRACT

Compositions, methods and apparatus (kits) for treating petroleum and petro-chemical based contaminants within expended filtration components, wherein the filtration components are exposed to water and a small concentrated volume of dormant bio-oxidizing medium comprising freeze-dried microorganisms on a freeze-dried substrate.

8 Claims, 3 Drawing Sheets

COMPOSITION, METHOD AND APPARATUS FOR SAFE DISPOSAL OF OIL CONTAMINATED FILTER

BACKGROUND OF THE INVENTION

Increased Federal, State and Local environmental regulations have produced an increased focus of environmental consciousness on a global level. The Environmental Protection Agency (EPA) along with the Occupational Safety and Health Administration (OSHA) have instituted increased and stringent regulations for the processing, manufacturing, utilization, and disposal of chemical compounds. For the purpose of this invention, the regulations of particular interest are those in the field of petroleum products, particularly those consisting of petroleum and petro-chemical based compounds (lubricating oils).

There are existing today numerous technologies for the reclamation and reprocessing of petroleum and petro-chemical compounds including the recovery of oil to be used in power stations and factories as an alternative source of fuel. When dealing with large volumes of these waste streams, there is a certain degree of technological and economic feasibility. One particular segment of this disposal market deals specifically with a variety of filtration components such as engine oil filter media and other filtration media utilized in automotive truck, marine and aircraft applications. These filtration media, when removed from the engine application, do represent petroleum and petro-chemical contaminated materials. These filtration media typically do not provide enough oil on a per unit basis to warrant a recycling activity and so pose a significant disposal problem. This problem is of particular importance in the face of increased environmental regulations which are imposed on large corporations.

SUMMARY OF THE INVENTION

One objective of the present invention is to provide compositions and methods which will facilitate safe disposal of oil contaminated filter media and preferably an accelerated decomposition of the petroleum products within the filter media, most preferably by natural biological decomposition.

Another objective of the present invention is to provide a method for the safe disposal of oil contaminated filter media which meets or exceeds current environmental regulations for disposal of such contaminated materials and which also provides a positive environmental impact.

An additional objective of the present invention is to provide a simple apparatus (kits) for treating contaminated filter media and filter housings to prevent the escape of petroleum and petro-chemical based contaminants therefrom for safe disposal.

Upon further study of the specification and appended claims, further objects and advantages of this invention will become apparent to those skilled in the art.

The present invention provides compositions, methods and apparatus for treating filtration components with petroleum or petro-chemical based compounds entrained therein to prevent leakage of these petroleum and petro-chemical based compounds into the environment. Preferred embodiments incorporate a bio-oxidizing medium which accelerates decomposition of these petroleum products.

In one aspect of the present invention, there are provided compositions capable of decomposing petroleum and petro-chemical based compounds which comprise a dormant bio-oxidizing medium capable of oxidizing petroleum and petro-chemical based compounds, preferably to $CO_2$ and water. This bio-oxidizing medium comprises freeze-dried microorganisms on a freeze-dried substrate. The freeze-dried microorganisms are capable of digesting petroleum or petro-chemical based compounds upon rehydration. The freeze-dried substrate and freeze-dried microorganisms are freeze-dried simultaneously.

In another aspect of this invention, there are provided methods for treating filtration components to prevent the escape of the petroleum and petro-chemical based contaminants entrained therein. These methods comprise exposing the entrained petroleum and petro-chemical based compounds to a dormant bio-oxidizing medium comprising freeze-dried microorganisms on a freeze-dried substrate as described above and water. The amount of water used rehydrates the freeze-dried substrate and freeze-dried microorganism so as to activate the freeze-dried microorganisms, and provides a source of oxygen for the activated microorganisms to digest petroleum and petro-chemical based compounds entrained within the filtration components. Preferably at least 40 ml water is added per gram of dormant bio-oxidizing used. The filtration component is then sealed to retain the petroleum, petro-chemical based compounds, bio-oxidizing medium and water therein so as not to escape into the environment. In preferred embodiments, at least 25%, most preferably at least 90%, of the entrained petroleum and petro-chemical based compounds are digested by the microorganisms.

In a further aspect of this invention, there are provided kits with which petroleum and petro-chemical based compounds entrained within filtration components can be treated. These kits comprise a written protocol which:

i) identifies at least one filtration component which can be treated, ii) identifies a bio-oxidizing medium to be added to a filtration component identified in the written protocol, iii) specifies an amount of water to be added to a filtration component identified in the written protocol, and iv) indicates the filtration component should be sealed after addition of the bio-oxidizing medium and water.

The kit also comprises a dormant bio-oxidizing medium and, optionally, a seal for a filtration component identified in the written protocol. The seal prevents the escape of entrained petroleum, petro-chemical based compounds, bio-oxidizing medium and water from the filtration component into the environment.

The compositions of this invention find wide use in decomposing petroleum and petro-chemical based compounds in many environments, while the methods and apparatus (kits) of this invention are well suited for treating filtration components having petroleum and petro-chemical based compounds entrained therein.

The "petro-chemical based compounds" referred to herein include aromatic hydrocarbons such as toluene and xylene, cresol, nitroaromatics, polychlorinated biphenols, greases, chlorinated aliphatics and aromatics and lipids.

The "filtration components" referred to herein include filter media, filter elements, filter housings and combinations thereof. Suitable filter media include those prepared from conventional materials using a conventional configuration such as a corrugated absorbent paper. Preferably, the filter media are within a filter housing. The filtration components are treated to prevent the escape of petroleum and petro-chemical based compounds entrained therein from escaping into the environment. This is accomplished by the methods of this invention which comprise:

a) exposing a filtration component contaminated with petroleum and/or petro-chemical based components, to a dormant bio-oxidizing medium as described above with sufficient water to reactivate said bio-oxidizing medium and provide a source of oxygen for the activated microorganisms to digest the petroleum and petro-chemical based compounds, and b) sealing the filtration component to prevent the escape of petroleum, petro-chemical based compounds, bio-oxidation medium and water from the filtration component into the environment.

The compositions, methods and apparatus (kits) of this invention can use a variety of microorganisms within the bio-oxidizing medium which decompose petroleum and petro-chemical based compounds. For example, bacteria conventionally known to digest petroleum compounds can be used as an active ingredient of the bio-oxidizing medium. There are several forms of bacillus which can be successfully colonized upon filter media with petroleum contaminants. Bacteria which grow rapidly and digest petroleum provide advantage in that colonization serves to increase the activity of the bio-oxidizing medium allowing adjustment to the level of contaminants within the filtration components.

The petroleum and petro-chemical based compounds within contaminated oil filters are sometimes complex and, as such, combinations of bacteria with or without enzymes can be effective in providing full degradation of the compounds to $CO_2$ and water. An example is the combination of bacillus, licehniformis (BAS50) and pseudomonas denitrificans used together with a dehydrogenase enzyme that serves as a catalyst for the removal of hydrogen atoms to assist in the decomposition and digestion of the petroleum compounds by the bacterium.

The rate and extent of decomposition by the microorganisms deployed for digestion of the petroleum compounds are, of course, important selection criteria; however, it is necessary that the microorganisms used can be freeze-dried and lie in a dormant state until exposed to water and petroleum material. The freeze-dried microorganisms of the dormant bio-oxidizing medium are used with a substrate which is also freeze-dried. The microorganisms are freeze-dried simultaneously with the substrate while supported thereon. A nutrient medium for the microorganism, i.e., such as corn syrup, agar or other protein food source, is preferably used as the substrate for the microorganism and forms a crystalline structure. These materials can readily be freeze-dried with the microorganisms supported thereon. These embodiments enable accelerated colonization upon rehydration due to the proximity of the nutrient source to the petroleum digesting bacteria.

The bio-oxidizing medium preferably contains a sufficient amount of freeze-dried nutrient to sustain the resuscitated microorganisms for at least one day in the absence of petroleum or petro-chemical based components. The amount of nutrient is preferably at least 0.1 gms per $10^7$ CFU (colony forming units) of microorganism.

Also of particular importance is the ability to activate/resuscitate freeze-dried microorganisms simply and easily such as by the addition of water. The addition of water will not only rehydrate the microorganisms and substrate to initiate growth and digestion of petroleum and petro-chemical based compounds, in preferred embodiments, it will also provide sufficient oxygen to sustain the microorganisms while digesting the petroleum and petro-chemical based compounds. Water is preferably used in an amount that forms a ratio of water to bio-oxidizing medium of at least 40 ml per gram of bio-oxidizing medium. Where the substrate comprises freeze-dried nutrients in crystalline form, the microorganisms have immediate access to the rehydrated nutrients, which enhances the number of viable microorganisms. Providing a concentrated bio-oxidizing medium with a large number of colony forming units will also increase the number of viable microorganisms. It is preferable to provide at least $10^5$ CFU of the microorganisms per gram of bio-oxidizing medium.

The substrate may include other components that assist in sustaining the microorganisms such as an oxygen source, i.e., methyl cellulose and titanium dioxide. Titanium dioxide is extremely photosensitive and, therefore, readily reacts in the presence of sunlight. Photon energy adsorbed onto the titanium dioxide layer induces oxygen to attach to the oil or petroleum based materials which facilitates and accelerates the oxidation of the oil compounds. Where the bio-oxidizing medium will not be exposed to light when digesting the petroleum compounds, $TiO_2$ will have little value.

Other substrate components used in the compositions, methods and apparatus (kits) of this invention are those which rehydrate in the presence of petroleum or petro-chemical based compounds and water. Suitable compounds fall within the group of polysaccharides, particularly celluloses or derivatives thereof derived from plant fibers.

The dormant bio-oxidizing media is preferably housed inside of a sealed container such as a polyurethane bag, a gelatin capsule, or similar enclosure, that is sufficiently sealed to prevent the introduction of moisture or oxygen present in ambient air so as to remain dormant. Where the container will dissolve in water at ambient temperature, such as a gelatin capsule, it need not be opened for use.

The bacteria are cultured on the substrate in solution to provide at least $10^5$ CFU (colony forming units) in solution. The microorganisms and substrate are then isolated by conventional techniques, such as centrifugation as described in "Molecular Cloning", $2^{nd}$ Ed. Cold Spring Harbor Press (1989) p. 1.77. The recovered microorganisms and substrate are then freeze-dried by conventional techniques, preferably with the use of liquid nitrogen.

It should be noted that this is the initial bacterium implant count not the colony count of the bacterium after exposure to the expended filter medium. The growth count is dependent on the amount of the petroleum and/or petro-chemical based contaminants within the filter media, as well as the amount of water and pH of the petroleum and petro-chemical based contaminants at the time of introduction.

The bio-oxidizing medium is preferably used in amounts of from about 15 wt. % to 30 wt. % of the contemplated, entrained petroleum and/or petro-chemical based compounds. For oil filters used in conventional automobile engines, the bio-oxidizing medium is typically used in an amount of from about 0.5 gm–2.0 gm. In preferred embodiments, the bio-oxidizing media are contained within gelatine capsules of less than 1.5 gms. These bio-oxidizing media typically have about $10^5$–$10^{12}$ CFU of the microorganisms and require at least 40 ml of added water to generate and sustain a hydrocatalytic reaction which causes the bio-oxidizing media to digest the petroleum and petro-chemical based compounds.

In certain embodiments, it may be desirable to also add to the filtration components a coagulant, thickening agent and/or polymer absorbent to prevent the escape of petroleum and petro-chemical based compounds into the environment. Initiators may also be added to aid activation and growth of the microorganisms. The thickeners are selected from a wide variety of compounds capable of absorbing petroleum and petro-chemical based compounds. The thickeners encompass both natural and synthetic compounds and in addition to kaolinite and magnesia include the families of the pillared clays, Fuller's earth, aluminas, starches, cellulose and granulated paper products such as paper pulp extracts and all forms of starches, haloysite, illite, monitmorillonite.

While compositions of the present invention are well suited for treatment of petroleum and petro-chemical based compounds within filtration components; they are not limited to such end uses. In preferred embodiments of this invention, the one or more microorganisms employed are obtained by selective pressure to consume the contaminants of interest. This is accomplished by growing a sample of the microorganism in a small amount of the contaminant, recovering the viable organisms and growing these organisms at higher concentrations of contaminant until microorganisms which grow in substantially undiluted contaminants, except for the added water, are obtained.

The kits of the present invention include a written protocol which identifies at least one filtration component which the kit can treat. The written protocol can vary widely in content from specifically identifying a model number or a product name, to a generic description of a "used filter", with the specific filters being identified by a picture, a code or other written indicia, a replacement filter for the expended filter to be treated or other physical identifier.

The written protocol will include other instructions with respect to the use of the individual components of the kit, such as, for example, the written protocol will identify a bio-oxidizing medium to be added to the filtration components with a specified amount of water. The written protocol will also indicate the filtration components should be sealed, after the bio-oxidizing medium and water are added thereto, in a manner which prevents the escape of the petroleum, petro-chemical based compounds, water and bio-oxidizing medium from the filtration components into the environment.

In addition to the written protocol, the kits of this invention include a dormant bio-oxidizing medium for treating the petroleum and/or petro-chemical based compounds within the filtration component, as described above. The bio-oxidizing medium is enclosed within a container to prevent premature activation. The container is preferably comprised of a material which is water soluble at a temperature of 25° C.

The kits of the present invention can also include, in addition to a bio-oxidizing medium, a coagulant, thickener and/or elastomer polymer absorbent or initiator as described above. These components can provide added advantage over the use of the bio-oxidizing medium alone in accelerating the decomposition of the petroleum and petro-chemical based compounds within the filtration components and reducing the risk of loss of petroleum products from the filter. However, significantly more material must be added to the filtration component, which can pose problems when the material must be introduced into a filter housing.

The kits provided by the present invention can also contain a seal for the filtration component or other means for retaining the petroleum and petro-chemical based compounds in the filtration components so as not to leak into the environment. The seals vary widely in configuration composition and operation. They can include separate containers such as a sealable bag which allows the treated filtration components to be placed inside and sealed therein. The material which forms the bag is preferably comprised of polyurethane or similar transparent synthetic, and is most preferably biodegradable. When the kit includes such a bag, the written protocol will indicate that the filtration components are to be inserted in the bag and sealed following treatment with the bio-oxidizing medium and water.

Where the filtration components include a filter housing, the seal can vary widely from an end cap for the open end of the filter housing, a plug that fills both the inlet and outlets of the filter housing or simply a film which covers the open end of the filter housing affixed to the filter by an elastomeric band or similar retaining means. The seal for the filtration components for retaining the petroleum and petro-chemical based compounds may be integrated with the container or box in which the replacement filters are packaged. For example, an end cap may be affixed to the inside of the packaging for a replacement filter, such as the cover of a box. The expended filter will be sealed when inserted in the packaging and closed. Alternatively, the packaging for the replacement filter itself may be adapted to function as a sealable container for the expended filter.

Other means for retaining the petroleum and petro-chemical based compounds in the filtration components vary widely and comprise the use of a coagulant, thickener, absorbent or other gelling component which seals the contents of a filter housing. Other means also comprise distorting a filter housing such as by crimping inlets and outlets or crushing the filter housing itself.

Another optional element of the kits provided by the present invention is a replacement filtration component for the filter component treated. Such a replacement can serve as a means for identifying the filtration component to be treated.

FIG. 1 illustrates a kit 50 of the present invention. Kit 50 comprises a written protocol 51 which identifies at least one filtration component for which the kit is suitable and identifies the bio-oxidizing medium 75 of the kit as a component to be added to an identified filtration component which is contaminated with petroleum and/or petro-chemical based components. Written protocol 51 is shown as a separate component but may be integrated into other optional components, such as a side panel of a box for a replacement filter. Bio-oxidizing medium 75 is shown within container 77 which is preferably a water soluble gelatine capsule.

Written protocol 51 also specifies a minimum amount of water to be added to the contaminated filtration component to which the bio-oxidizing medium 75 has been added. Such an amount may be specified with instructions to "fill" the filtration component, such as a filter housing with water. The written protocol also will indicate that the expended filtration component with bio-oxidizing medium and water added thereto be sealed to retain the petroleum, petro-chemical based compounds, added water and added bio-oxidizing medium therein. In preferred embodiments, the written protocol will identify a seal for the expended filtration component or other means for retaining the petroleum, petro-chemical based compounds, added water and added bio-oxidizing medium within the filtration component.

Written protocol 51 can have other indications, depending on the contents of bio-oxidizing media 75, and can comprise more than one writing. Bio-oxidizing medium 75 can be placed in more than one container and the components thereof can be placed in separate containers. For example, a portion of the nutrient medium can be incorporated in a separate container, although not preferred.

Kit 50 may also include other components such as a seal for the filter housing such as an end cap 131, shown in FIG. 5a, plug 132, shown in FIG. 5b, or film 133 with elastomeric band 134, shown in FIG. 5c. Alternatively, the kit may include a sealable bag 135 with seal 20, shown in FIG. 5d to house the filtration component or the kit may include a thickener and/or coagulant to be added to the filtration component which prevents the escape of petroleum by forming a gel.

FIG. 2a illustrates a kit 10 which is another embodiment of the present invention. Kit 10 comprises a replacement filter component 15 with filter media 30 and filter housing 31. Also included in kit 10 is bio-oxidizing medium 75, as defined above, shown in a gelatine capsule 77. Kit 10 further includes written protocol 100 which, at a minimum, identifies the filtration components for which the kit is suitable, identifies bio-oxidizing medium 75 as a component to be added to an identified filtration component which is contaminated, specifies an amount of water to be added to the filtration component to which the bio-oxidizing medium is added and indicates the filtration components be sealed to prevent the escape of petroleum and petro-chemical based components from the filtration component to the environment. The components of these kits may be separately packaged, transported and/or stored. The amount of water specified can be a simple instruction to fill a filter housing with water.

FIG. 2b illustrates an alternative configuration for kit 10, wherein written protocol 100 appears on a package 101 for the replacement filter 15 and bio-oxidizing medium 75 in gelatin capsule 77.

FIGS. 3a and 3b illustrate kits 20 and 30 of this invention, respectively, wherein a seal for a filter housing is provided. In FIG. 3a, the seal comprises film 133 and elastomeric band 134. Written protocol 51 appears on film 133. In FIG. 3b, the seal comprises end cap 131 with written protocol 51 appearing thereon.

FIG. 4 illustrates end cap 136 as a seal, which is integrated with package 101 for a replacement filter. Written protocol 51 appears on package 101.

The method of this invention for treating filtration components with petroleum and petro-chemical based compounds entrained therein comprises exposing filter media having petroleum and petro-chemical based compounds entrained therein to a dormant bio-oxidizing medium as described above and an amount of water which rehydrates the freeze-dried microorganisms and freeze-dried nutrient substrate, preferably crystalline, and provides a source of oxygen for the activated microorganism to digest the petroleum and petro-chemical based compounds within the filtration components. The filtration component is then sealed to retain the petroleum, petro-chemical based compound, bio-oxidizing medium and water therein so as not to escape into the environment. Where a coagulant is present, additional water may be necessary to form a solid or gel with the petroleum and/or petro-chemical based contaminants within the filtration component. It may be necessary to disperse the bio-oxidizing medium, coagulant, water and residual oil by agitation.

Petroleum digestion commences upon contact or exposure of the contaminants to the microorganisms and water. The added water activates the bio-oxidizing medium and provides oxygen for the microorganism. Preferably, the water within the sealed container will provide sufficient oxygen to sustain the petroleum digesting bacteria until the petroleum and petro-chemical based compounds are oxidized to $CO_2$ and water. These biochemical reactions and reproduction cycles preferably continue until the filter medium approaches an equilibrium meaning that all of the petroleum products and nutrients have been digested and decomposed by the bacteria and there is no longer a sufficient food source to sustain the life of the petroleum digesting bacteria. In preferred embodiments, the filter media is digested as well.

EXAMPLES

An analysis of the biodegradability of a sample of waste oil with a dehydrated bacterial culture is performed as follows:

The chemical oxygen demand (COD) of a sample (0.010 mls) of waste oil is first determined to approximate the extent of oxidation necessary to consume all of the waste oil. The COD analysis is performed per Standard Methods 18th ed. Method 5220D "Closed Reflux Colorimetric Method". The waste oil samples (0.010 mls) are dissolved in 0.10 mls of chloroform and diluted to 10 mls with deionized water. A blank is prepared with 0.10 mls of chloroform and diluted to 10 mls with deionized water. Six replicants are set up, the low and high values dropped, and the remaining four values averaged to obtain an average COD of 1,397,600 mg/l. std. dev. 235,327 mg/l.

The biological oxygen demand (BOD) of waste oil samples seeded with dehydrated bacteria culture is determined as follows. A sample of waste oil (0.010 mls) is pipetted onto the side of a 300 ml BOD bottle and swirled to disperse along the side. Dilution water was prepared according to OECD Guidelines Method 301b and added to the bottles to approximately ¾ full. Two mls of seed are pipetted directly onto the oil sample to ensure contact. The seed is prepared by dissolving 0.623 grams of a combination of dehydrated BAS 50 and pseudomonas denitrificans on dehydrated methyl cellulose and nutrient in 300 mls of deionized water and stirring for 1 hour prior to use. The BOD bottle is then filled to the neck with dilution water. The initial dissolved oxygen is taken and the bottle capped. The replicants are set up, the high and low values dropped and the remaining eight values averaged after 5 days, 15 days and 28 days. The average BOD values are reported in Table 1 below, and the % biodegradability values are determined from the average COD values.

Examples of values are reported in Table 1 below.

TABLE 1

| Incubation | 5 days | 15 days | 28 days |
| --- | --- | --- | --- |
| Average BOD | 34,700 mg/L | 76,400 mg/L | 159,800 mg/L |
| Average COD | 1,397,600 mg/L | 1,397,600 mg/L | 1,397,600 mg/L |
| % Biodegradability | 2.5% | 5.5% | 11.4% |

The results show that the dehydrated bacteria on a freeze-dried substrate can be activated/resuscitated rapidly with the addition of water and will grow/digest in the presence of the waste oil.

BRIEF DESCRIPTION OF THE DRAWINGS

Various other features and attendant advantages of the present invention will be more fully appreciated as the same becomes better understood when considered in conjunction with the accompanying drawings, in which like reference characters designate the same or similar parts throughout the several views, and wherein.

Figure 1:
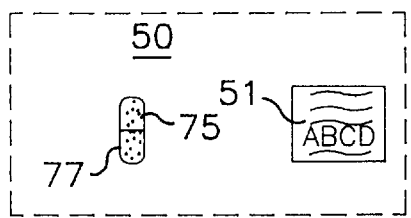
FIG. 1 illustrates a kit of the present invention for treating petroleum and petro-chemical based compounds within filtration components.
Figure 2A:
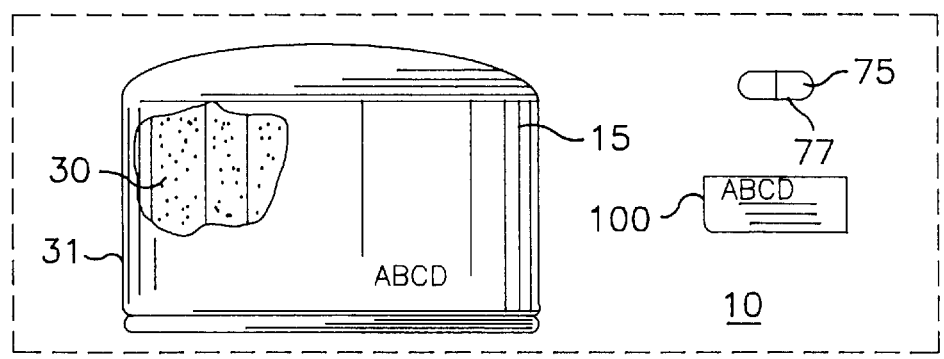
FIGS. 2a and 2b illustrate another kit of the present invention for treating petroleum and petro-chemical based compounds within filtration components.
Figure 2B:
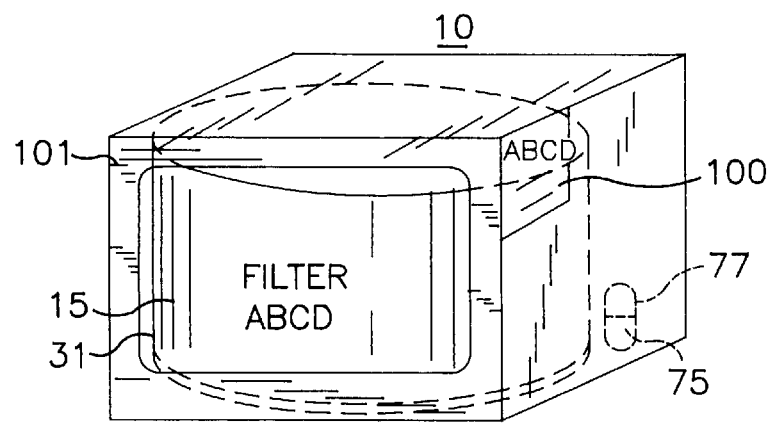
Figure 3A:
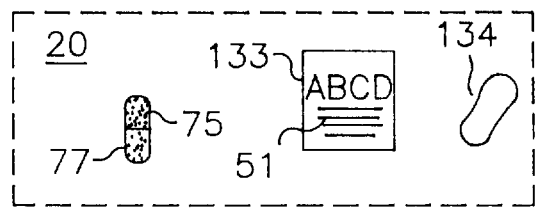
FIGS. 3a and 3b illustrate kits of the present invention with optional seals.
Figure 3B:
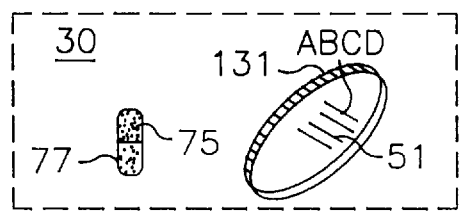
Figure 4:
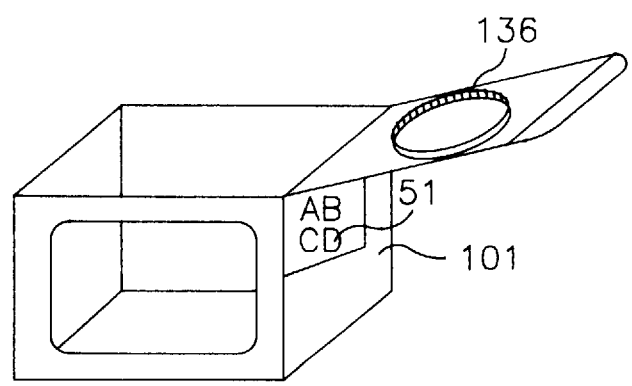
FIG. 4 illustrates a seal incorporated in the replacement filter packaging used in kits and methods of this invention.
Figure 5A:
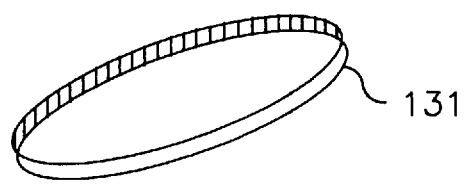
FIGS. 5a–5c each illustrate a different seal for use in the kits and methods of this invention.
Figure 5B:
Figure 5C:
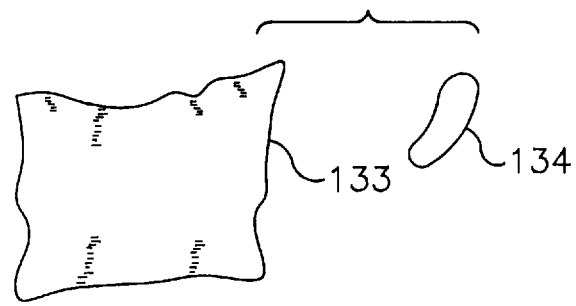
Figure 5D:
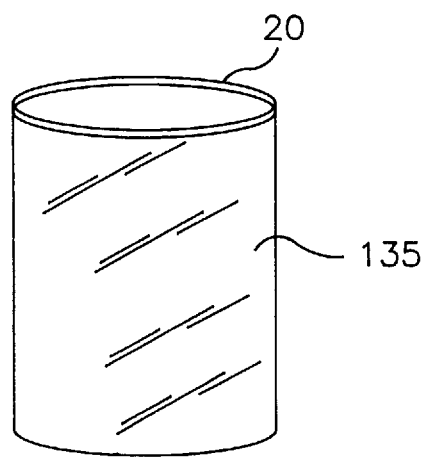
FIG. 5d is a transparent bag which can be used in the kits and methods of this invention to prevent the escape of petroleum and petro-chemical based compounds into the environment.

From the foregoing description, one skilled in the art can easily ascertain the essential characteristics of this invention, and without departing from the spirit and scope thereof, can make various changes and modifications of the invention to adapt it to various usages and conditions.

The subject matter of copending applications Ser. No. 08/742,849, filed Nov. 1, 1996, and Ser. No. filed simultaneously herewith (attorney Dkt. No. DANA 68P1), assigned to the same assignee, are hereby incorporated by reference.

What is claimed is:

1. A kit for treating filtration components with petroleum and/or petro-chemical based compounds entrained therein which comprises:
   a) a written protocol which
      i) identifies at least one filtration component for which the kit is suitable for treatment,
      ii) identifies a bio-oxidizing medium to be added to a filtration component identified in the written protocol,
      iii) specifies an amount of water to be added to a filtration component with the bio-oxidizing medium added thereto and
      iv) indicates a filtration component with water and bio-oxidizing medium added thereto is to be sealed in a manner which prevents the escape of petroleum, petro-chemical based compounds, bio-oxidizing medium and water therein into the environment; and
   b) a dormant bio-oxidizing medium identified within the written protocol comprising freeze-dried microorganisms on a freeze-dried substrate wherein said freeze-dried microorganisms are capable of digesting the petroleum and petro-chemical based compounds entrained within a filtration component upon rehydration.

2. A kit as in claim 1, wherein said freeze-dried substrate is a freeze-dried nutrient for said microorganism in an amount sufficient to sustain the microorganism once resuscitated for at least 1 day in the absence of petroleum or petro-chemical based compounds.

3. A kit as in claim 2, wherein said bio-oxidizing medium additionally contains a component selected from coagulants, thickeners and polymer absorbents.

4. A kit as in claim 3, which additionally contains a seal for the filtration component.

5. A kit as in claim 4, wherein the seal is selected from the group consisting of end caps for an open end of said filtration component, plugs for the inlets and outlets of a filtration component and films in combination with elastomatic bands of a size which covers an open end of said filtration component.

6. A kit as in claim 4 which additionally comprises a replacement filtration component which conforms to a filtration component identified in said written protocol.

7. A kit as in claim 1 which additionally comprises a sealable bag of a size sufficient to hold the filtration components identified in the written protocol, said written protocol additionally indicating that the filtration components be sealed by inserting said filtration component into a sealable bag.

8. A kit as in claim 1 wherein the bio-oxidizing medium additionally comprises a gel forming component selected from the group consisting of coagulants, thickeners, polymer absorbents and combinations thereof and said written protocol indicates the filtration components be sealed by forming a gel within the filtration component with said gel forming component and water.

* * * * *